(12) United States Patent
Boroczky et al.

(10) Patent No.: US 10,219,767 B2
(45) Date of Patent: Mar. 5, 2019

(54) CLASSIFICATION OF A HEALTH STATE OF TISSUE OF INTEREST BASED ON LONGITUDINAL FEATURES

(71) Applicant: KONINKLIJKE PHILIPS N.V., Eindhoven (NL)

(72) Inventors: Lilla Boroczky, Mount Kisco, NY (US); Rafael Wiemker, Kisdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 5 days.

(21) Appl. No.: 15/516,512

(22) PCT Filed: Sep. 29, 2015

(86) PCT No.: PCT/IB2015/057433
§ 371 (c)(1),
(2) Date: Apr. 3, 2017

(87) PCT Pub. No.: WO2016/059493
PCT Pub. Date: Apr. 21, 2016

(65) Prior Publication Data
US 2018/0220985 A1 Aug. 9, 2018

Related U.S. Application Data

(60) Provisional application No. 62/062,977, filed on Oct. 13, 2014.

(51) Int. Cl.
*G06K 9/00* (2006.01)
*A61B 6/00* (2006.01)
(Continued)

(52) U.S. Cl.
CPC .......... *A61B 6/5217* (2013.01); *A61B 5/0035* (2013.01); *A61B 5/7275* (2013.01); *A61B 5/7485* (2013.01); *A61B 6/032* (2013.01); *A61B 6/037* (2013.01); *G06F 19/00* (2013.01); *G06T 7/0014* (2013.01); *G06T 7/0016* (2013.01); *G16H 50/20* (2018.01); *A61B 5/0033* (2013.01);
(Continued)

(58) Field of Classification Search
None
See application file for complete search history.

(56) References Cited

U.S. PATENT DOCUMENTS 6,466,687 B1 10/2002 Uppaluri et al.
7,298,881 B2 11/2007 Giger et al.
(Continued)

FOREIGN PATENT DOCUMENTS

WO 2010115885 A1 10/2010
WO WO2014102661 * 7/2014

*Primary Examiner* — Stephen P Coleman (57) ABSTRACT

A method includes determining, with a computer implemented classifier, a health state of tissue interest of a subject in at least one pair of images of the subject based on a predetermined set of longitudinal features of the tissue of interest of the subject in the at least one pair of images of the subject. The at least one pair of images of the subject includes a first image of the tissue of interest acquired at a first moment in time and a second image of the tissue of interest acquired at a second moment in time. The first and second moments in time are different moments in time. The method further includes visually displaying indicia indicative of the determined health state.

13 Claims, 4 Drawing Sheets

(51) Int. Cl.
| | |
|---|---|
| *A61B 5/00* | (2006.01) |
| *G06T 7/00* | (2017.01) |
| *A61B 6/03* | (2006.01) |
| *G16H 50/20* | (2018.01) |
| *G06F 19/00* | (2018.01) |
| *A61B 5/055* | (2006.01) |

(52) U.S. Cl.
CPC ............ *A61B 5/055* (2013.01); *A61B 5/7267* (2013.01); *A61B 6/5235* (2013.01); *G06T 2207/10072* (2013.01); *G06T 2207/10132* (2013.01); *G06T 2207/20081* (2013.01); *G06T 2207/30004* (2013.01)

(56) References Cited

U.S. PATENT DOCUMENTS

| | | |
|---|---|---|
| 7,912,528 B2 | 3/2011 | Krishnan et al. |
| 8,295,575 B2 | 10/2012 | Feldman et al. |
| 8,442,285 B2 | 5/2013 | Madabhushi et al. |
| 2004/0101181 A1 | 5/2004 | Giger et al. |
| 2008/0081365 A1 | 4/2008 | Borok et al. |
| 2011/0129129 A1* | 6/2011 | Avinash .................. A61B 5/04 382/128 |
| 2011/0173027 A1 | 7/2011 | Olszewski et al. |
| 2011/0274338 A1 | 11/2011 | Park et al. |
| 2012/0081386 A1 | 4/2012 | Wiemker et al. |
| 2015/0045651 A1 | 2/2015 | Craomoceamm et al. |
| 2015/0317792 A1 | 11/2015 | Wiemker et al. |

* cited by examiner

CLASSIFICATION OF A HEALTH STATE OF TISSUE OF INTEREST BASED ON LONGITUDINAL FEATURES

CROSS-REFERENCE TO PRIOR APPLICATIONS

This application is the U.S. National Phase application under 35 U.S.C. § 371 of International Application No. PCT/IB2015/057433, filed on Sep. 29, 2015, which claims the benefit of U.S. Provisional Application No. 62/062,977, filed on Oct. 13, 2014. These applications are hereby incorporated by reference herein.

The following generally relates to computer-aided diagnosis (CADx) and more particularly to classifying a health state of tissue of interest of a subject based on longitudinal features in a pair of images of the subject and non-image based clinical information, and is described with particular application to computed tomography (CT). However, other imaging modalities, such as ultrasound (US), positron emission tomography (PET), magnetic resonance imaging (MRI), are contemplated herein.

Despite encouraging trends in cancer survival and advances in cancer treatments, diagnosis of cancer at an early stage tends to be crucial for positive prognosis. On the other hand, false-positive diagnosis of cancer could lead to unnecessary procedures with possible complications, over-treatment, patient anxiety, avoidable costs, etc. Computer-aided diagnosis (CADx) systems can aid clinicians in diagnosing various cancers, such as lung, breast, prostate, etc., with a goal to improve the clinicians'(e.g. radiologists) diagnostic performance.

CADx systems have used image data from a single imaging modality or from a combination of multiple different imaging modalities to aid clinicians. Examples of such imaging modalities have included ultrasound (US), computed tomography (CT), positron emission tomography (PET), magnetic resonance imaging (MRI), etc. Non-imaging data, such as demographics, medical and family history, risk factors, molecular and genetic tests, has also been used. Unfortunately, CADx systems have provided aid based on only a current imaging study.

By way of example, when a radiologist identifies an abnormality (e. g. lung nodule) in a current lung image of a patient, the radiologist needs to render a recommendation for subsequent action, such as a biopsy of the identified nodule or an imaging follow-up on a certain time interval. A lung cancer CADx system would process the current image (and optionally non-image data) and produce a result based thereon that would aid the radiologist in forming a diagnosis for the patient on the current image.

Aspects described herein address the above-referenced problems and others.

In one aspect, a method includes determining, with a computer implemented classifier, a health state of tissue interest of a subject in at least one pair of images of the subject based on a predetermined set of longitudinal features of the tissue of interest of the subject in the at least one pair of images of the subject. The at least one pair of images of the subject includes a first image of the tissue of interest acquired at a first moment in time and a second image of the tissue of interest acquired at a second moment in time. The first and second moments in time are different moments in time. The method further includes visually displaying indicia indicative of the determined health state.

In another aspect, a computing system includes a memory that stores instructions of an image data processing module, and a processor that executes the instructions. The processor, executing the instructions, classifies a health state of tissue interest of a subject in at least one pair of images of the subject based on a predetermined set of longitudinal features of the tissue of interest of the subject in the at least one pair of images of the subject. The at least one pair of images of the subject includes a first image of the tissue of interest acquired at a first moment in time and a second image of the tissue of interest acquired at a second moment in time. The first and second moments in time are different moments in time. The processor, executing the instructions, further visually displays indicia indicative of the determined health state.

In another aspect, a computer readable storage medium is encoded with computer readable instructions. The computer readable instructions, when executed by a processer, causes the processor to: receive a training data set of pairs of images of the tissue, wherein each pair includes images acquired at different moments in time, and wherein a first sub-set of the training data includes a first known health state of the tissue and at least a second sub-set of the training data includes at least a second known and different health state of the tissue, register the images in the training data set, identify the tissue of interest in the registered training data set images, trend a predetermined set of longitudinal features of the tissue of interest in the registered training data set images, select a sub-set of the set of features representing a set of relevant features, and create the classifier based on the training data set and the selected sub-set of the set of features, wherein the classifier includes one or more sub-classifiers.

The invention may take form in various components and arrangements of components, and in various steps and arrangements of steps. The drawings are only for purposes of illustrating the preferred embodiments and are not to be construed as limiting the invention.

Figure 1:
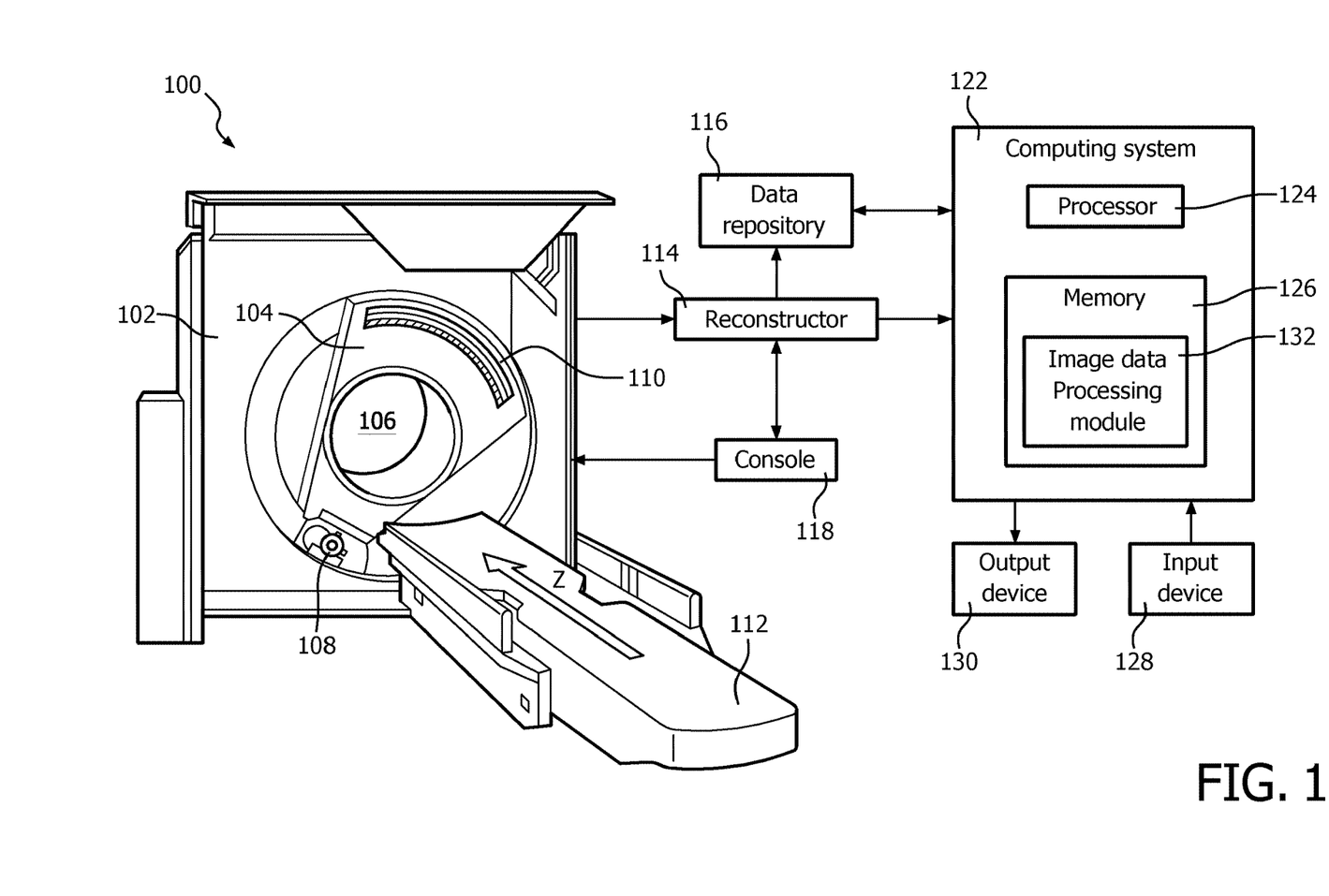
FIG. 1 schematically illustrates a computing system, with an image data processing module, in connection with an imaging system.

FIG. 1 illustrates an imaging system 100, such as a computed tomography (CT) scanner.

In another embodiment, the imaging system 100 includes a different imaging modality such as ultrasound (US), positron emission tomography (PET), single photon emission tomography (SPECT), X-ray, magnetic resonance imaging (MRI), etc. imaging system. Another embodiment includes more than one (same or different) imaging system 100, including an individual imaging system and/or a hybrid imaging system with two different modalities.

The illustrated imaging system 100 includes a generally stationary gantry 102 and a rotating gantry 104, which is rotatably supported by the stationary gantry 102 and rotates around an examination region 106 about a z-axis. A radiation source 108, such as an x-ray tube, is rotatably supported by the rotating gantry 104, rotates with the rotating gantry 104, and emits radiation that traverses the examination region 106.

A detector array 110 subtends an angular arc opposite the examination region 106 relative to the radiation source 108, detects radiation that traverses the examination region 106, and generates projection data indicative thereof. A subject support 112, such as a couch, supports a subject or object in the examination region 106 and is movable in coordination with scanning.

A reconstructor 114 reconstructs the projection data, generating image data. A data repository 116 stores image data from the imaging system 100 and/or other imaging system. Examples of repositories include a picture archiving and communication system (PACS), a radiology information system (RIS), a hospital information system (HIS), an electronic medical record (EMR), a database, a server, etc. The data can be transferred via Digital Imaging and Communications in Medicine (DICOM), Health Level 7 (HL7), etc.

A general-purpose computing system serves as an operator console 118. The console 118 includes one or more processors that execute one or more computer readable instructions (software) stored or encoded in computer readable storage medium local or remote to the system 100. Software resident on the console 118 allows the operator to control operation of the system 100 such as selecting an imaging protocol, initiating scanning, etc.

A computing system 122 includes at least one processor 124 (e.g., a microprocessor, a central processing unit, etc.) that executes at least one computer readable instruction stored in computer readable storage medium ("memory") 126, which excludes transitory medium and includes physical memory and/or other non-transitory medium. The microprocessor 124 may also execute one or more computer readable instructions carried by a carrier wave, a signal or other transitory medium. The instruction, in this example, includes an image data processing module 132.

As described in greater detail below, the image data processing module 132, in one instance, executes the instruction, which causes the processor 124 to processes image data acquired at least two different times (e.g., an initial acquisition and a follow-up acquisition three month later), extract longitudinal features or changes in characteristics of a tissue of interest (e.g., a tumor) therefrom, and employ the extracted longitudinal features to determine a health state (e.g., benign or malignant, degree of malignancy, etc.) of the tissue of interest.

Examples of longitudinal features include a change in a volume, a change in a texture, a change in a composition, a change in a shape, a change in a margin, etc. Other longitudinal changes and/or characteristics are also contemplated herein. Such information may indicate a probability of a particular health state. As such, the computing system 122 can provide improved results, relative to a configuration that processes only a current image, and not also an early acquired image.

In another embodiment, the image data processing module 132 can determine a health state of only a prior acquired image, of only a current image, and/or of a combination of the prior acquired and current image, and visually present, via an output device 130, one or more of the three results, which can be observed and/or reviewed by a clinician. The clinician can then see the trend of changes from a point of view of the module 132. The module 132 can additionally process non-image data.

The computing system 122 further includes an output device(s) 130 such as a display monitor, a filmer, etc., and an input device(s) 128 such as a mouse, keyboard, etc. The computing system 122 can be separate from the imaging system 100 (as shown), part of the console 118, and distributed across systems. It is to be appreciated that in one instance the computing system 122 can be part of and/or form a computer-aided diagnosis (CADx) system.

Figure 2:
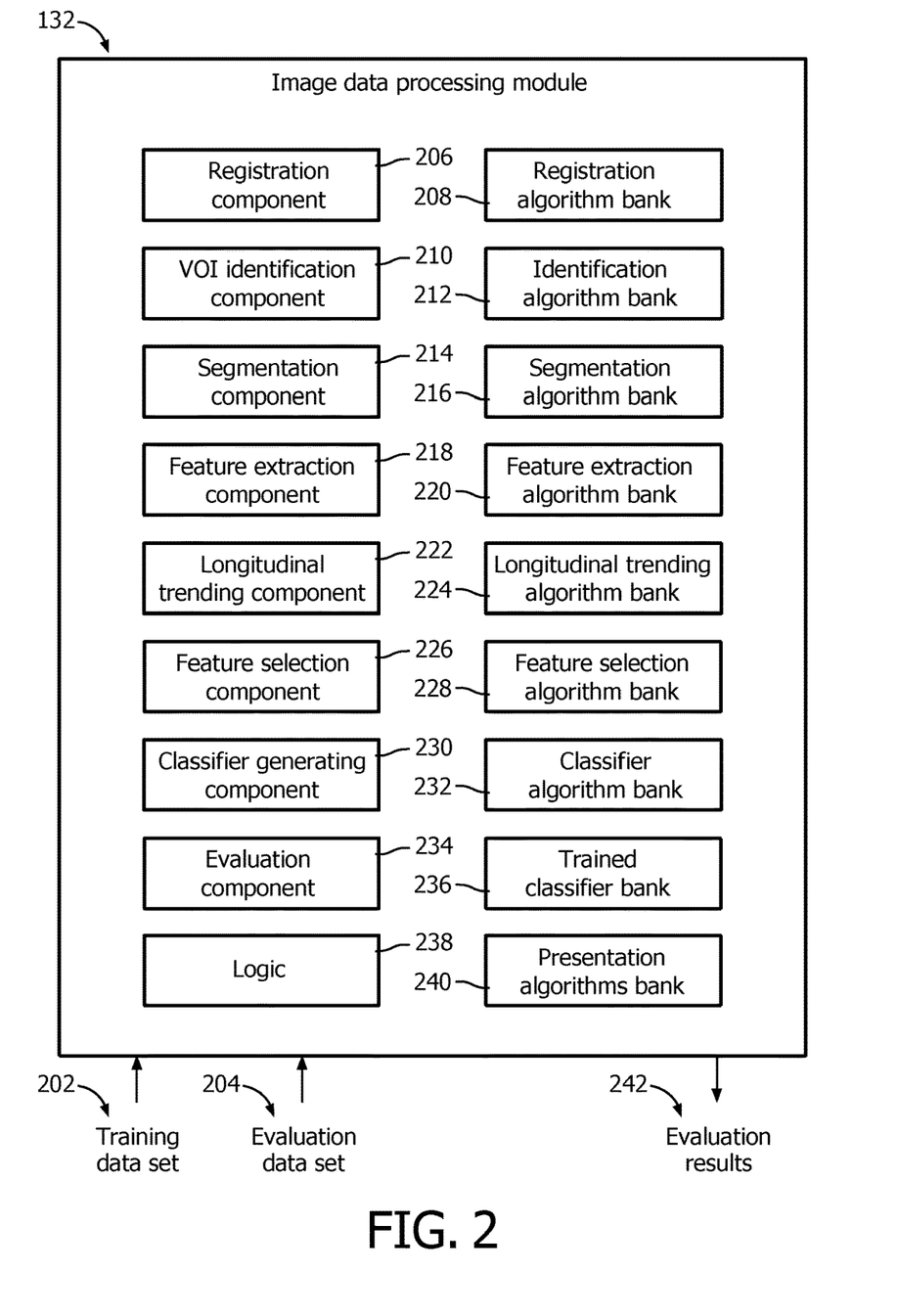
FIG. 2 schematically illustrates an example of the image data processing module.

FIG. 2 schematically illustrates an example of the image data processing module 132.

The image data processing module 132 receives, as input, one or more training data sets 202 and an evaluation data set 204. The one or more training data sets 202 are used to train a classifier(s) based at least on longitudinal features, or the changes of the longitudinal features and/or characteristics of tissue of interest. The one or more training data sets 202 include image pairs corresponding to images of a volume including the tissue of interest and images of the volume without the tissue of interest, the images in both cases acquired at two different points in time. The one or more training data sets 202 may also include non-image data.

The evaluation data set 204 includes an image pair, for example, a previously acquired image and a currently acquired image of a patient, which is evaluated using the trained classifier(s). In one instance, the two acquisitions correspond to an initial and follow up (e.g., 3 months later) acquisition, for example, where the tissue of interest is suspected to include a tumor such as cancer. The evaluation data set 204 may also include non-image data. Example of non-image data includes demographics, medical history, family history, risk factors, molecular test results, genetic test results, etc.

The image data processing module 132 further includes a registration component 206. The registration component 206 spatially co-registers the images in the one or more training data sets 202 and the images in the evaluation data set 204. In the illustrated embodiment, the registration component 206 employs an algorithm from a registration algorithm bank 208, which includes known and/or other registration techniques, including affine and/or elastic transformations. Affine transformations, generally, are linear transformations and include rotation, scaling, translation, etc., and elastic transformations, generally, also allow warping and include radial basis functions, physical continuum models, large deformation models, etc.

The image data processing module 132 further includes a volume of interest (VOI) identification component 210. The VOI identification component 210 identifies one or more VOIs in the co-registered images of the one or more training data sets 202 and the evaluation data set 204. In one instance, the VOI identification component 210 employs an automated approach, using a computer-aided detection approach. With this approach, the VOI identification component 210 employs an algorithm from an identification algorithm bank 212, which includes known and/or other identification techniques. In another instance, the VOI identification component 210 utilizes user input. In yet another instance, the VOI identification component 210 utilizes a combination of an automated approach and user input.

The image data processing module 132 further includes segmentation component 214. The segmentation component 214 segments the identified VOIs in the co-registered images of the one or more training data sets 202 and the evaluation data set 204. In the illustrated embodiment, the segmentation component 214 employs an algorithm from a segmentation algorithm bank 216, which includes known and/or other registration techniques, including an automated, manual or semi-automatic (e.g., a computer generates an initial contour and the user modifies it) three-dimensional (3D) segmentation approach.

The image data processing module 132 further includes a feature extraction component 218. The feature extraction component 218 extracts features from segmented regions and/or the surrounding tissue of interest of the one or more training data sets 202 and the evaluation data set 204. In the illustrated embodiment, the feature extraction component 218 employs an algorithm from a feature extraction algorithm bank 220, which includes known and/or other feature extraction techniques.

Examples of suitable features include, but are not limited to, shape (e.g. round, oval, irregular, etc.), margin (e.g. smooth, spiculated, etc.), texture (e.g. solid, semi-solid or non-solid nodules), vascular features of tissue surrounding tissue of interest (e.g., vascular features of the vessels surrounding a nodule), organ architectural features (e.g., organ shape and parenchymal analysis), tissue of interest co-existence (e.g., total number of nodules, spatial distribution, constellation, etc.), co-morbidity features (emphysema, chronic obstructive pulmonary disease (COPD), etc.), as well as one or more other features.

An example feature extraction algorithm is described in application Ser. No. 12/441,950, entitled "Advanced computer-aided diagnosis of lung nodules", and filed Sep. 18, 2007, which is incorporated herein by reference in its entirety. Another example feature extraction algorithm is described in application Ser. No. 13/061,959, entitled "System and method for fusing clinical and image features for computer-aided diagnosis", and filed Sep. 9, 2009, which is also incorporated herein by reference in its entirety. Other approaches for extracting features are also contemplated herein.

The image data processing module 132 includes a longitudinal trending component 222. With respect to training, the longitudinal trending component 222 calculates longitudinal trends for the one or more training data sets 20, including for the images and/or non-image information therein. In one instance, this includes calculating a difference for feature values or a percentage change, or assigning values of categorical changes, such as changing from solid to non-solid nodule as "1". In the illustrated embodiment, the longitudinal trending component 222 employs an algorithm from a longitudinal trending algorithm bank 224, which includes known and/or other longitudinal trending techniques.

The image data processing module 132 further includes a feature selection component 226. With respect to training, the feature selection component 226 applies a feature selection algorithm from a feature selection algorithm 228, which identifies a set of most relevant features from the all possible features using a training dataset and a chosen classifier. Examples of suitable algorithms include, but are not limited to an exhaustive search, a genetic algorithm, a forward or backward elimination algorithm, etc.

The image data processing module 132 further includes a classifier generating component 230. With respect to training, classifier generating component 230 builds and trains, using the selected features, one or more classifiers to estimate of the health state of the tissue of interest. In the illustrated embodiment, the classifier generating component 230 employs an algorithm from a classifier algorithm bank 232, which includes known and/or other classifier techniques. Examples of suitable classifiers include, but are not limited to, linear regression, logistic regression, support vector machines, decision tree, etc. Ensembles of classifiers include, but are not limited to, ensembles of decision trees such as a random forest.

The image data processing module 132 further includes an evaluation component 234. With respect to evaluation, the evaluation component 234 employs one or more of the created and trained classifiers to determine a health state of the tissue of interest from the images of the evaluation data set 204. The evaluation component 234 generates a signal indicative of the evaluation results (i.e., a health state score or indicia indicative thereof). When using an ensemble for evaluation, the health state can be derived as the majority of the health state estimates, an average of the health state estimates, etc.

The image data processing module 132 further includes logic 238. With respect to evaluation, the logic 238 formats and outputs the signal. The signal can be visually presented via a display monitor of an output device 130 and/or conveyed to another device. In the illustrated embodiment, the logic 238 employs an algorithm from a presentation algorithms bank 240. For example, with one algorithm, the logic 238 visually presents a numerical score. For example, the score may be in a range from 0.0 to 1.0, where a score of 0.0 indicates an absence of a disease (e.g., a tumor is benign) where a score of 1.0 indicates a presence of the disease (e.g., a tumor is malignant).

In another example, the logic 238 visually presents the score with color coding and graphical indicia. For instance, in one example, the score is visually presented as a traffic light based on thresholding the score into three distinct colors (green: e.g. score<0.25; yellow: score between 0.25 and 0.75; red: score>0.75). In another instance, the score is visually presented as a continuous color bar (e.g., from green through yellow to orange to red; green representing a score of 0.0, and red representing a score of 1.0). In another example, the logic 238 visually presents the score on a background of a disease distribution of other (anonymized) cases, potentially stratified by geographic regional, age, sex, risk-type, co-morbidities.

Figure 3:
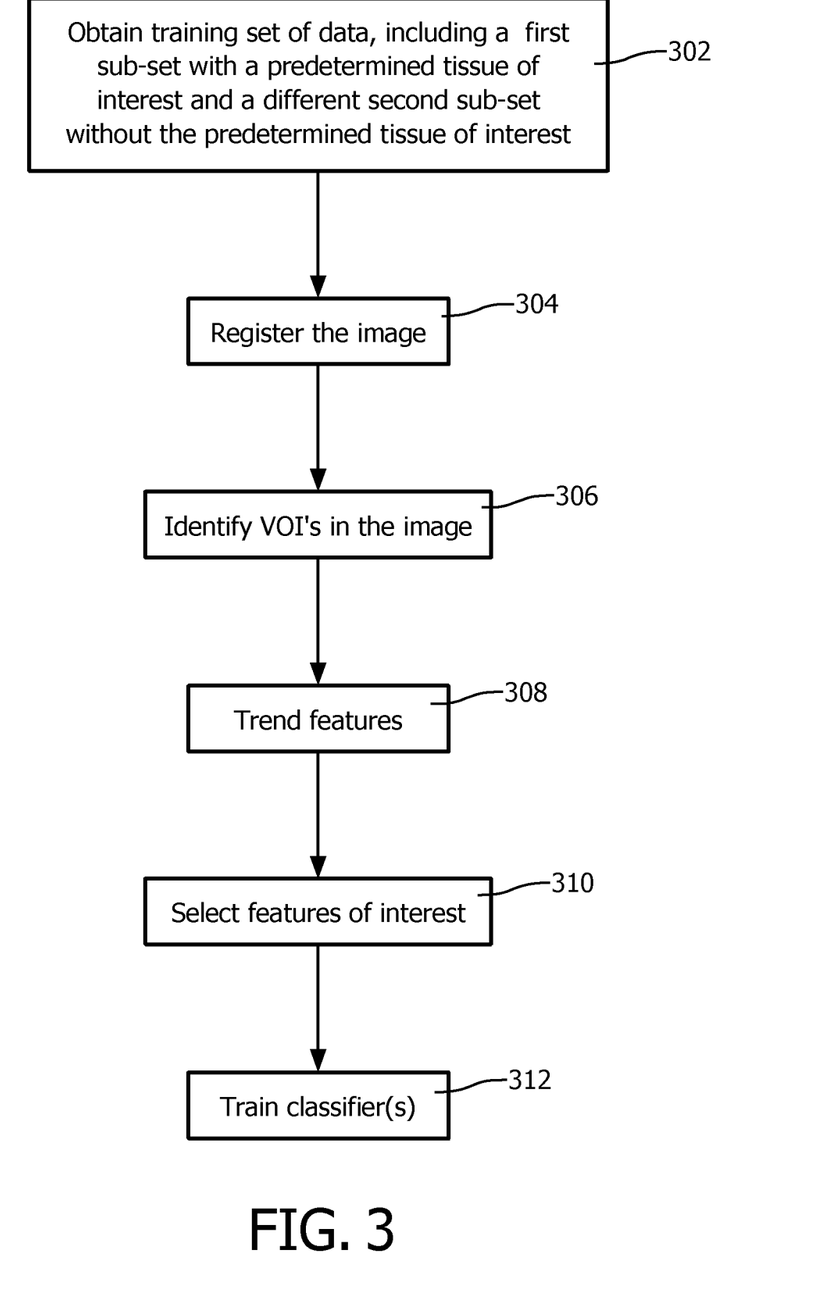
FIG. 3 illustrates an example method for training one or more classifiers to determine a health state of tissue of interest based on longitudinal features of a training data set.

FIG. 3 illustrates an example method for creating one or more classifiers based on longitudinal features.

It is to be appreciated that the ordering of the acts is not limiting. As such, other orderings are contemplated herein. In addition, one or more acts may be omitted and/or one or more additional acts may be included.

At 302, a training data set is obtained.

As described herein, this includes a sub-set of image pairs (e.g., previously and currently acquired) with tissue of interest (e.g., a tumor) and a different sub-set of image pairs (e.g., previously and currently acquired) without the tissue of interest.

At 304, the images are registered.

At 306, one or more volumes of interest are identified in the registered images.

At 308, a set of features is trended for the volumes of interest.

At 310, a sub-set of the set of features is selected.

At 312, one or more classifiers are created and trained using the training data set and the sub-set of features, as described herein and/or otherwise.

Optionally, non-image data may additionally be used to create and train the one or more classifiers.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 4:
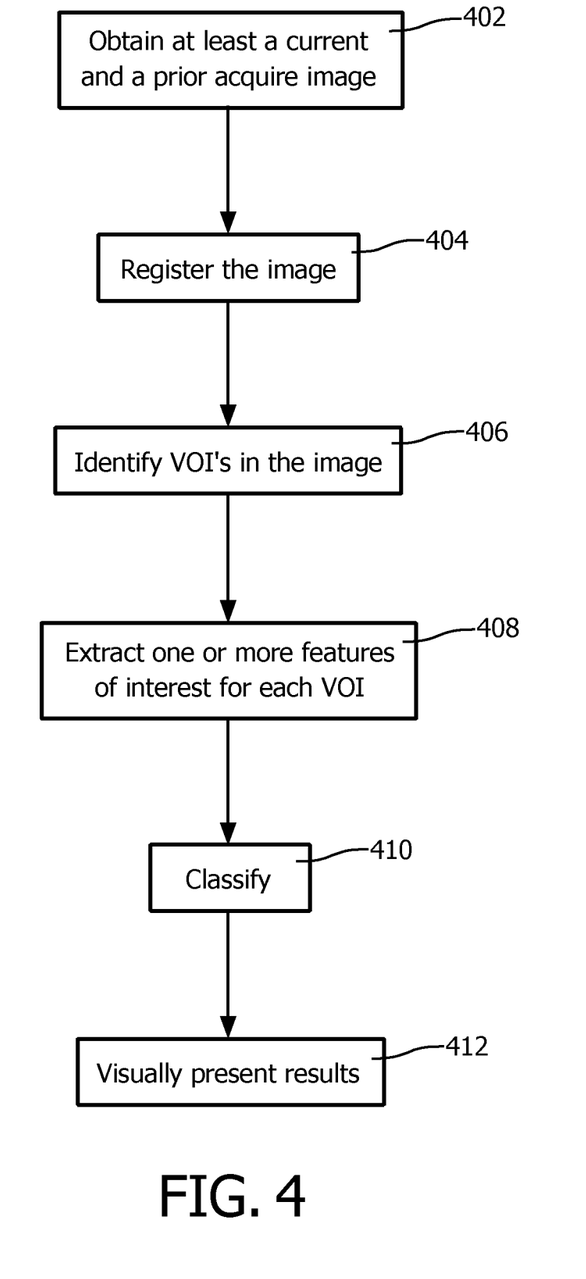
FIG. 4 illustrates an example method for employing the one or more classifiers to determine the health state of tissue of interest based on longitudinal features of an evaluation data set.

FIG. 4 illustrates an example method for employing the one or more classifiers of FIG. 3 based on longitudinal features.

It is to be appreciated that the ordering of the acts is not limiting. As such, other orderings are contemplated herein.

In addition, one or more acts may be omitted and/or one or more additional acts may be included.

At 402, an evaluation data set is obtained.

As described herein, this includes at least one pair of images of a region acquired at different moments in time (e.g., 3 months apart).

At 404, the images are registered.

At 406, one or more volumes of interest are identified in the registered images.

At 408, a predetermined set of features is extracted from each volumes of interest.

Optionally, non-image data may be obtained.

At 410, a classifier is used to evaluate the evaluation data set based on the extracted predetermined set of features.

At 412, the results are visually presented.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   registering at least one pair of images of a subject, wherein the at least one pair of images of the subject includes a first image of a tissue of interest acquired at a first time and a second image of the tissue of interest acquired at a second different time;
   identifying at least one volume of interest of the subject based on a training data set of pairs of images of training tissue acquired at different times, wherein a first sub-set of the training data set includes a first known health state of the training tissue and at least a second sub-set of the training data set includes at least a second known health state of the training tissue;
   extracting a set of longitudinal features from the at least one volume of interest, wherein the longitudinal features are changes in characteristics of the volume of interest of the subject between the first time and the second time;
   determining, with a computer implemented classifier, a health state of the volume of interest based on the set of longitudinal features extracted from the volume of interest; and
   visually displaying indicia indicative of the determined health state.

2. The method of claim 1, wherein the set of longitudinal features of the tissue of interest includes one or more of a change in a shape of the tissue of interest, a change in a margin of the tissue of interest, a change in a texture of the tissue of interest, a change in a vascularity of the tissue of interest, a change in an architecture of the tissue of interest, a co-existence of the tissue of interest, or a co-morbidity of the tissue of interest.

3. The method of claim 1, wherein the training data set is generated by:
   receiving the training data set of pairs of images of the training tissue;
   registering the images in the training data set;
   identifying the tissue of interest in the registered training data set images;
   trending a predetermined set of longitudinal features of the tissue of interest in the registered training data set images;
   selecting a sub-set of the set of features representing a set of relevant features; and
   creating and training the classifier based on the training data set and the selected sub-set of the set of features, wherein the classifier includes one or more sub-classifiers.

4. The method of claim 3, further comprising:
   obtaining non-image data about the subject; and
   determining the health state of tissue interest by classifying the extracted set of longitudinal features and the non-image data.

5. The method of claim 4, further comprising:
   trending the predetermined set of longitudinal features by determining a difference of a feature between a pair of images.

6. The method of claim 1,
   wherein determining the health state of the volume of interest comprises classifying the extracted set of longitudinal features.

7. The method of claim 6, further comprising:
   obtaining non-image data about the subject;
   wherein determining the health state of the volume of interest further comprises classifying the non-image data.

8. The method of claim 7, wherein the non-image data includes one or more of demographics, medical history, family history, risk factors, molecular test results, or genetic test results.

9. The method of claim 1, further comprising:
   determining a numerical score, in a predetermined range of numerical scores, based on the determined health state in which a first score of the range indicates an absence of an disease and a second score of the range indicates a presence of the disease, wherein visually displaying the indicia includes visually displaying the numerical score.

10. The method of claim 9, wherein the numerical score indicates a severity of the disease.

11. The method of claim 9, further comprising:
    creating a map that maps different sub-ranges of the predetermined range of numerical scores to different levels of severity and different colors; and
    visually displaying graphical indicia with a color indicative of the score based on the map.

12. The method of claim 11, wherein the health state distribution is stratified by at least on of geographic regional, age, gender, risk-type, or co-morbidity.

13. A computing system, comprising:
    a memory that stores instructions of an image data processing module; and
    a processor that executes the instructions, which causes the processor to:
    register at least one pair of images of a subject, wherein the at least one pair of images of the subject includes a first image of a tissue of interest acquired at a first time and a second image of the tissue of interest acquired at a second different time;
    identify at least one volume of interest of the subject based on a training data set of pairs of images of training tissue acquired at different times, wherein a first sub-set of the training data set includes a first known health state of the training tissue and at least a second sub-set of the training data set includes at least a second known health state of the training tissue;

extract a set of longitudinal features from the at least one volume of interest, wherein the longitudinal features are changes in characteristics of the volume of interest of the subject between the first time and the second time;

classify a health state of the volume of interest based on the set of longitudinal features extracted from the volume of interest; and visually display indicia indicative of the classified health state.

* * * * *